US008007457B2

(12) United States Patent
Taylor

(10) Patent No.: US 8,007,457 B2
(45) Date of Patent: Aug. 30, 2011

(54) ELASTICIZED GARMENT AND STRAPPING SYSTEM TO AID IN BODY MOBILITY SUPPORT AND MAINTENANCE

(75) Inventor: Beverly Cusick Taylor, Telluride, CO (US)

(73) Assignee: TheraTogs, Inc., Telluride, CO (US)

( * ) Notice: Subject to any disclaimer, the term of this patent is extended or adjusted under 35 U.S.C. 154(b) by 1113 days.

(21) Appl. No.: 10/526,320

(22) PCT Filed: Aug. 30, 2003

(86) PCT No.: PCT/US03/27023
§ 371 (c)(1),
(2), (4) Date: Feb. 25, 2005

(87) PCT Pub. No.: WO2004/019812
PCT Pub. Date: Mar. 11, 2004

(65) Prior Publication Data
US 2006/0000478 A1 Jan. 5, 2006

(51) Int. Cl.
*A61F 13/06* (2006.01)
(52) U.S. Cl. .................... 602/75; 2/69; 602/78
(58) Field of Classification Search ............. 2/450, 459, 2/22, 16, 67, 69, 114, 228, 238, 400–403, 2/455, 461–463, 466; 602/75, 78; 450/8
See application file for complete search history.

(56) References Cited

U.S. PATENT DOCUMENTS

| | | | | |
|---|---|---|---|---|
| 3,559,654 A | | 2/1971 | Pope | 128/519 |
| 3,888,244 A | * | 6/1975 | Lebold | 602/4 |
| 4,843,647 A | * | 7/1989 | Phillips et al. | 2/69 |
| 4,917,109 A | | 4/1990 | Ruge | 128/874 |
| 4,971,073 A | * | 11/1990 | Schneider | 128/874 |
| 5,036,838 A | | 8/1991 | Sherman | 128/155 |
| 5,144,694 A | * | 9/1992 | Conrad Da oud et al. | 2/69 |
| 5,146,932 A | | 9/1992 | McCabe | 128/873 |
| 5,274,852 A | | 1/1994 | Hogan | 2/114 |
| 5,376,130 A | | 12/1994 | Courtney | 623/33 |
| 5,398,340 A | * | 3/1995 | Kibbee | 2/2.5 |
| 5,403,268 A | * | 4/1995 | Clement | 602/20 |

(Continued)

OTHER PUBLICATIONS

Prior designs by applicant, "The Pacesetter" (6 pgs) limited distribution by assignee hereof 1999, 2000, 2001 {Attachments B1 & B2 of applicant's U.S. Appl. No. 60/407,035}.

(Continued)

*Primary Examiner* — Patricia M Bianco
*Assistant Examiner* — Camtu T Nguyen
(74) *Attorney, Agent, or Firm* — Macheledt Bales LLP

(57) ABSTRACT

A therapeutic garment system for use on a mammalian body, and associated method of donning, whereby the garments are adapted for donning and releasably securing in a close-fitting fashion so that a plurality of elasticized pieces may be releasably applied, utilizing fasteners, against an outwardly facing surface of at least one—and more often two—of the garments in an operative therapeutic configuration. At least one elasticized garment is included for donning around an area of a torso such as the upper-torso, lower-torso, or full-torso area; a second elasticized garment is included for donning and releasably securing in a close-fitting fashion around a portion of the body, other than that around which the first garment will (or has been) be donned. In addition to an outwardly facing surface adapted for accepting releasable fasteners, each garment has an under-layer with an inwardly facing surface to resist slippage. A wide variety of operative therapeutic configurations are available to one donning garment system components, including those that address generally targeted objectives.

23 Claims, 9 Drawing Sheets

U.S. PATENT DOCUMENTS

| | | | |
|---|---|---|---|
| 5,561,932 A * | 10/1996 | Bracken | 40/638 |
| 5,582,583 A | 12/1996 | Ballantyne | 602/5 |
| 5,599,286 A | 2/1997 | Labelle et al. | |
| 5,628,725 A * | 5/1997 | Ostergard | 602/62 |
| 5,754,982 A * | 5/1998 | Gainer | 2/2.5 |
| 5,782,790 A | 7/1998 | Allen | 602/75 |
| 5,829,058 A | 11/1998 | Dicker et al. | 2/69 |
| 5,830,165 A * | 11/1998 | Rowe et al. | 602/4 |
| 5,857,990 A * | 1/1999 | Maas | 602/62 |
| 5,891,187 A | 4/1999 | Winthrop et al. | 607/96 |
| 5,902,261 A * | 5/1999 | Schwartz | 602/61 |
| 5,957,873 A | 9/1999 | Allen | 602/19 |
| 6,086,551 A | 7/2000 | Allen | 602/19 |
| 6,088,831 A * | 7/2000 | Jensen et al. | 2/2.5 |
| 6,109,267 A | 8/2000 | Shaw et al. | 128/882 |
| 6,240,882 B1 | 6/2001 | Gross | 119/850 |
| 6,283,124 B1 | 9/2001 | Schleuning et al. | 128/845 |
| 6,338,723 B1 | 1/2002 | Carpenter et al. | 602/75 |
| 6,398,746 B2 * | 6/2002 | Bramlage et al. | 602/5 |
| 6,440,094 B1 * | 8/2002 | Maas | 602/5 |
| 6,440,159 B1 | 8/2002 | Edwards et al. | 607/108 |
| 6,860,789 B2 | 3/2005 | Bell et al. | 450/20 |
| 6,936,021 B1 * | 8/2005 | Smith | 602/19 |
| 6,945,945 B2 | 9/2005 | Givler et al. | 602/20 |
| 7,871,388 B2 * | 1/2011 | Brown | 602/19 |
| 2002/0077578 A1 | 6/2002 | Bonutti | 602/75 |

OTHER PUBLICATIONS 2 pgs background technical information printed Mar. 2003 from www.adeli-suit.com about "Adeli Suit" {as noted in applicant's U.S. Appl. No. 60/320,025 filed Mar. 19, 2003}.

\* cited by examiner

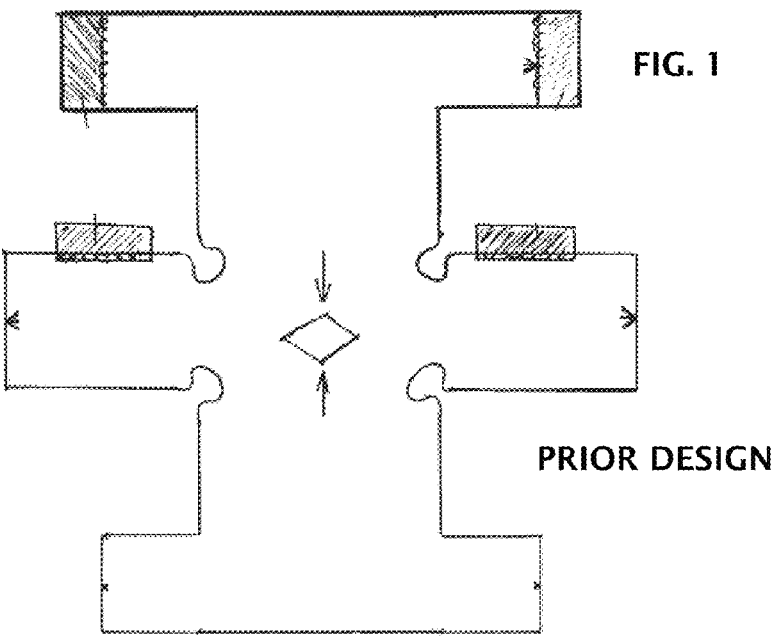
FIG. 1
PRIOR DESIGN
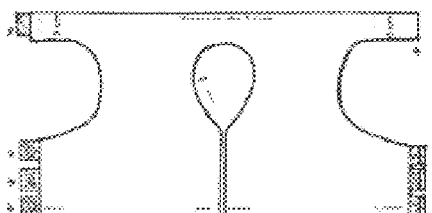
FIG. 2A
PRIOR DESIGNS
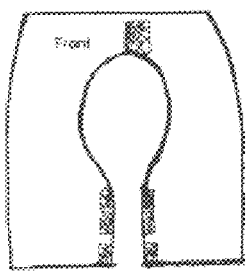 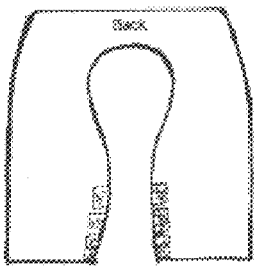
FIG. 2B  FIG. 2C
FIG. 3
PRIOR DESIGN
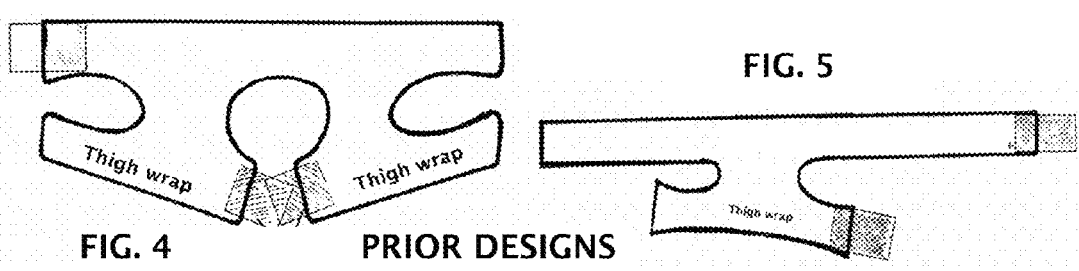
FIG. 4  PRIOR DESIGNS  FIG. 5

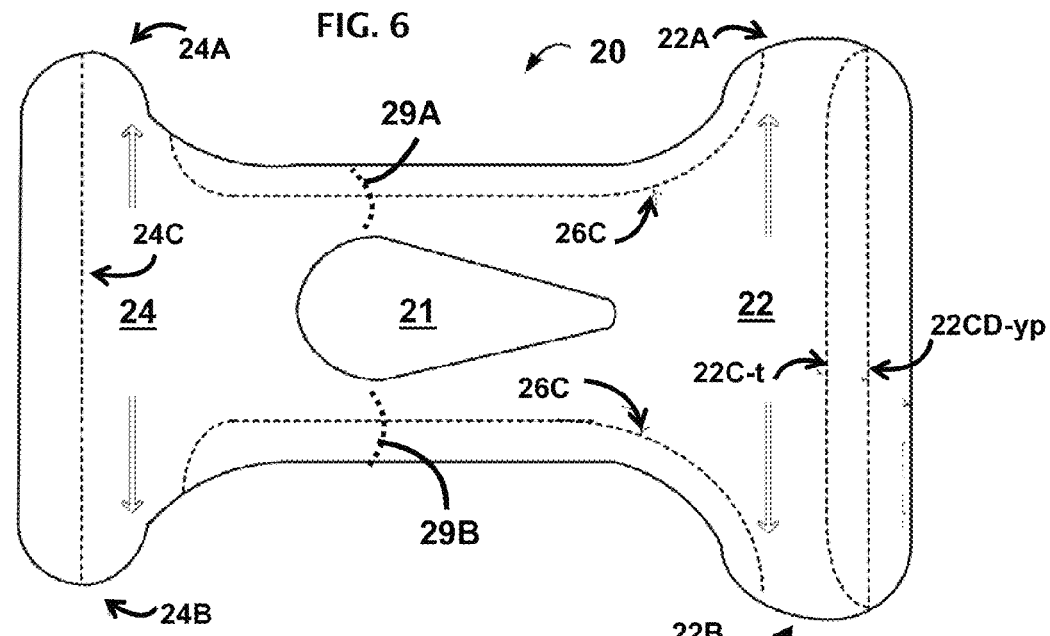
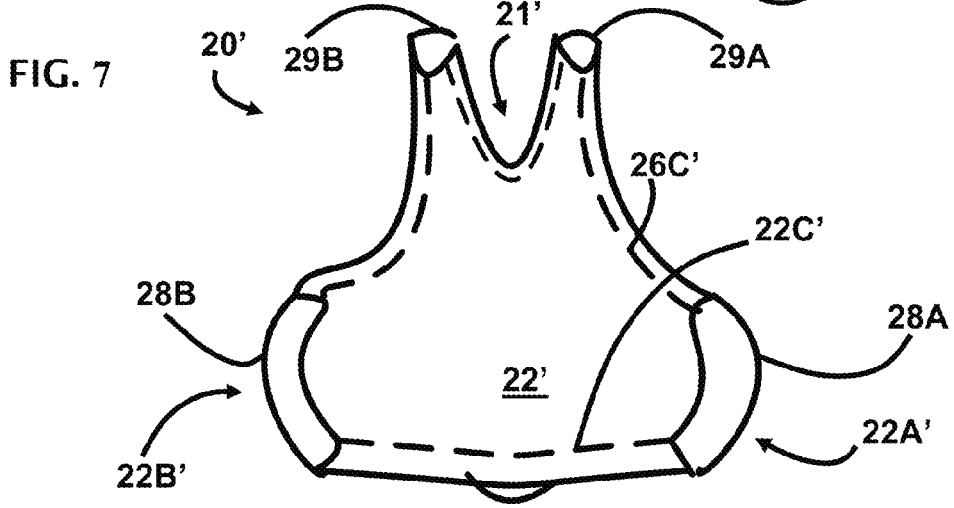
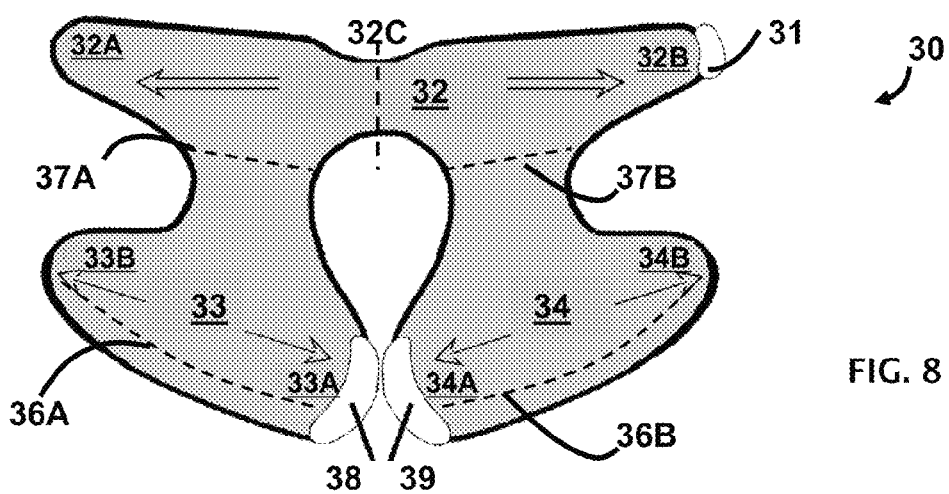

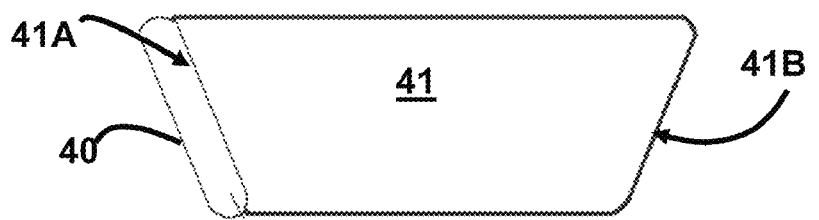
FIG. 9
FIG. 10
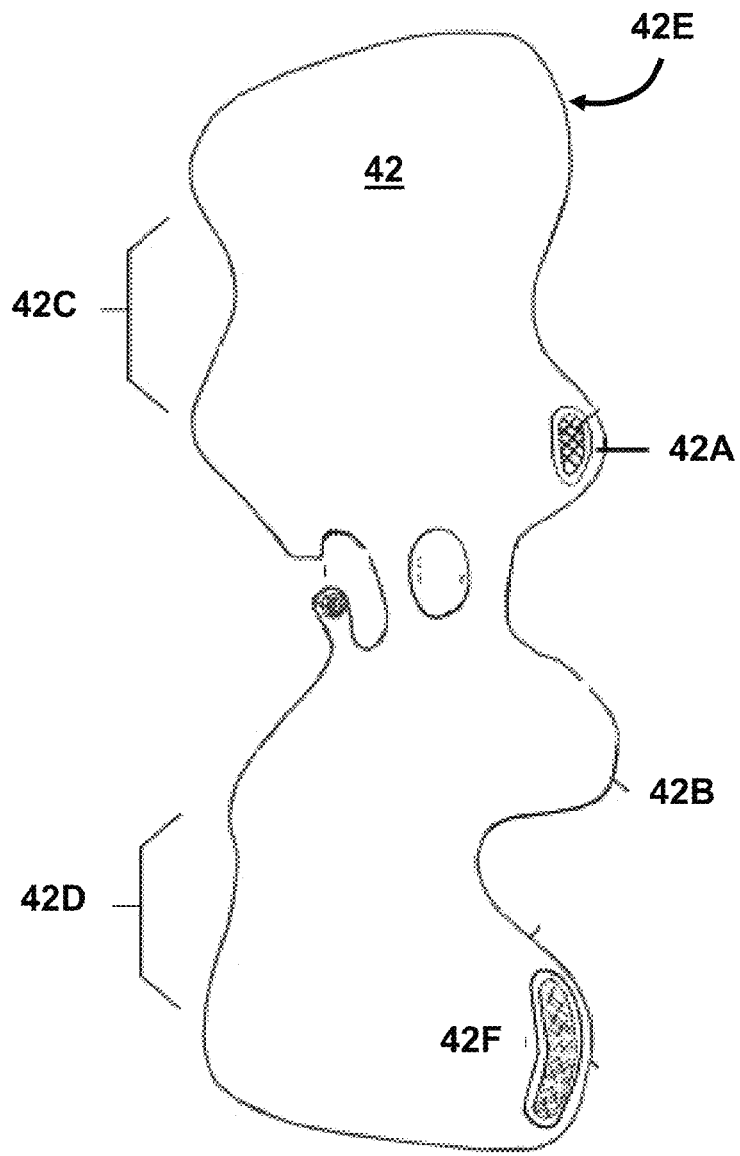

FIG. 11
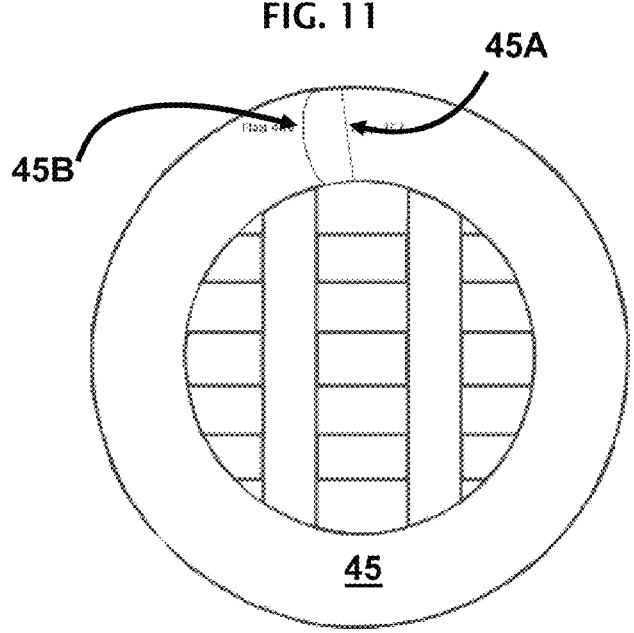
FIG. 12
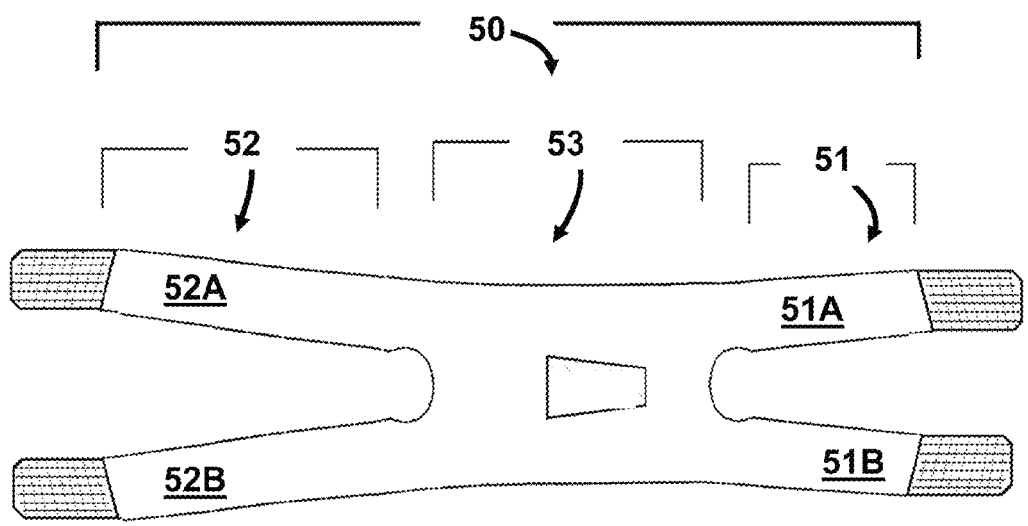
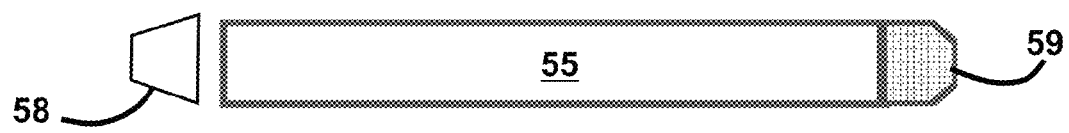
FIG. 13

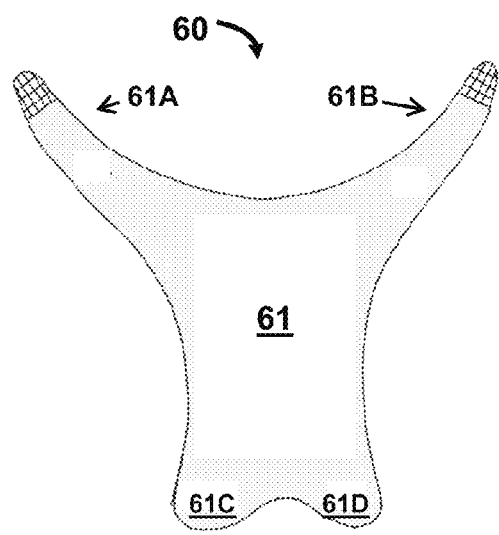
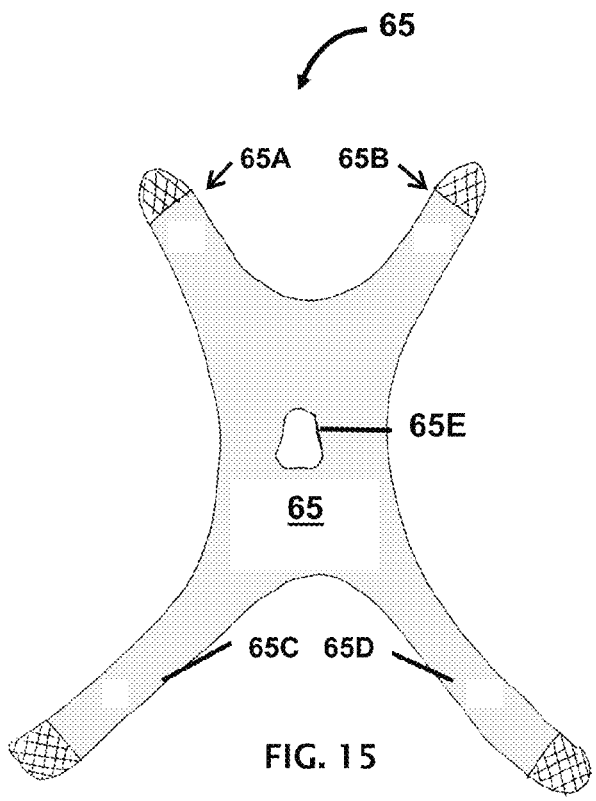
FIG. 14
FIG. 15
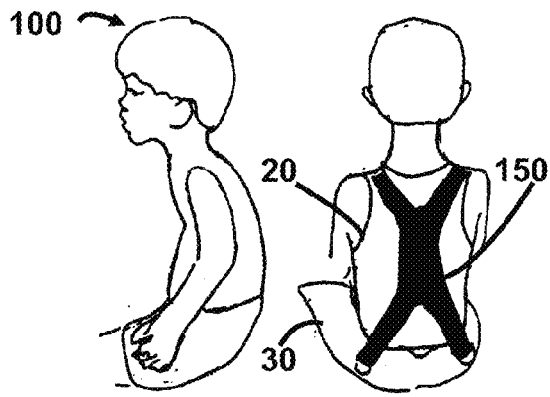
FIG. 16A   FIG. 16B
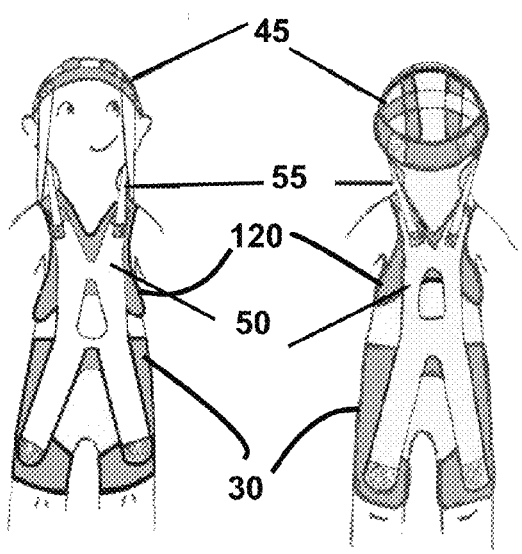
FIG. 17A   FIG. 17B

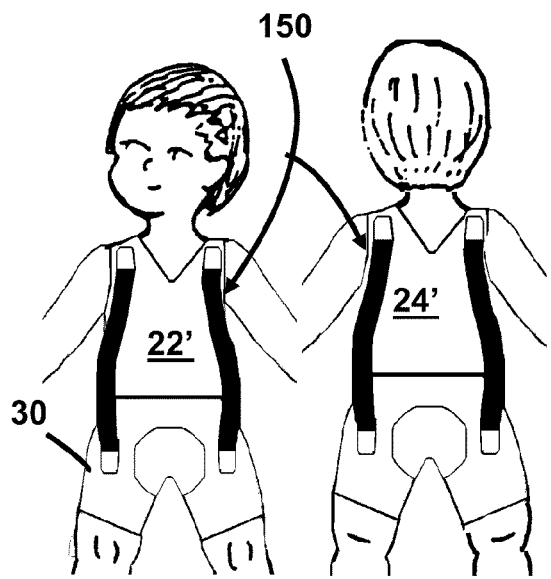
FIG. 18A    FIG. 18B
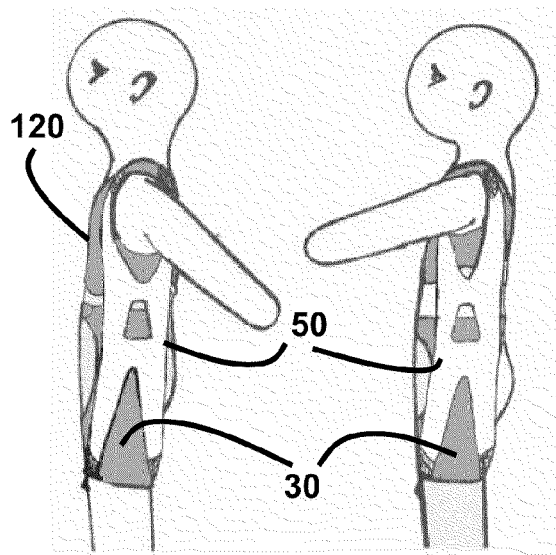
FIG. 19A    FIG. 19B
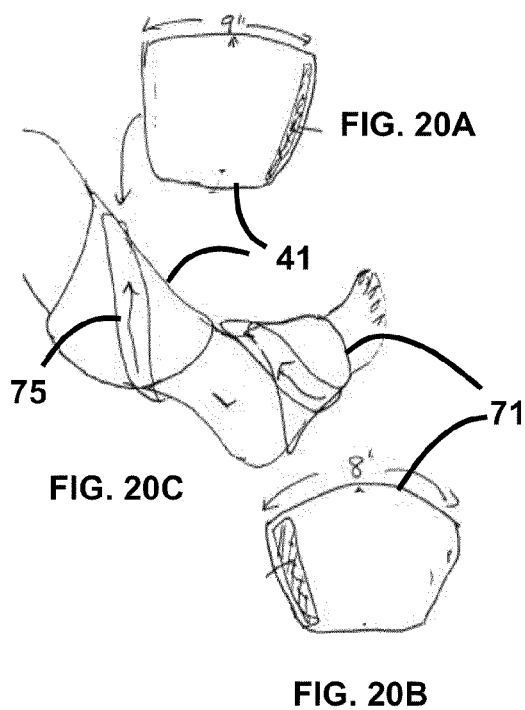
FIG. 20A
FIG. 20C
FIG. 20B
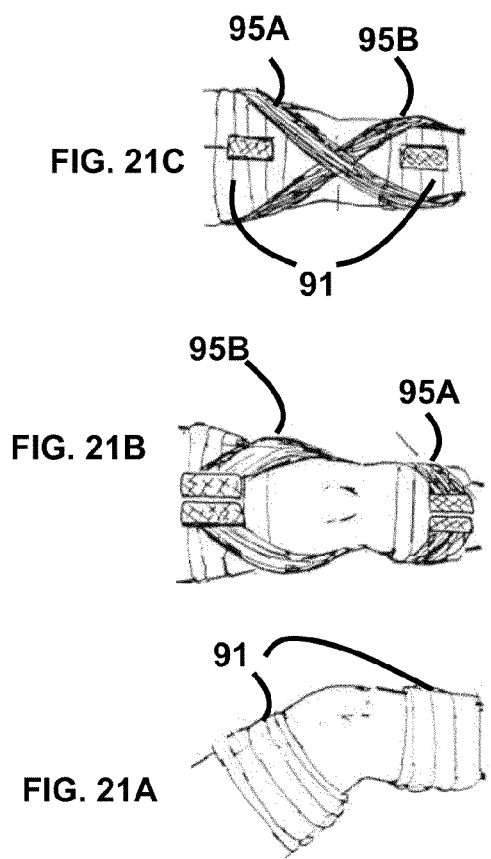
FIG. 21C
FIG. 21B
FIG. 21A

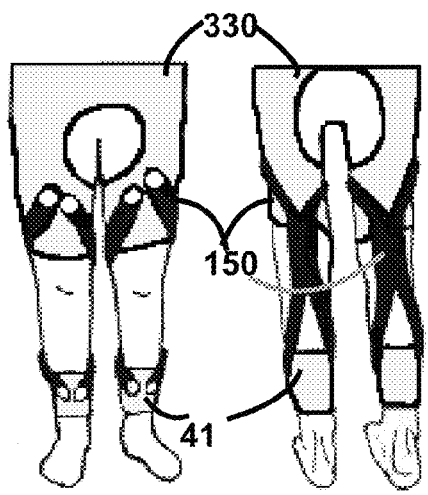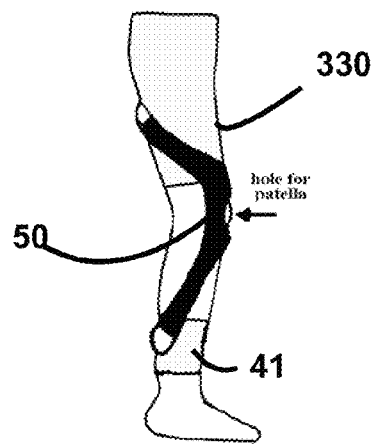
FIG. 22A  FIG. 22B  FIG. 23
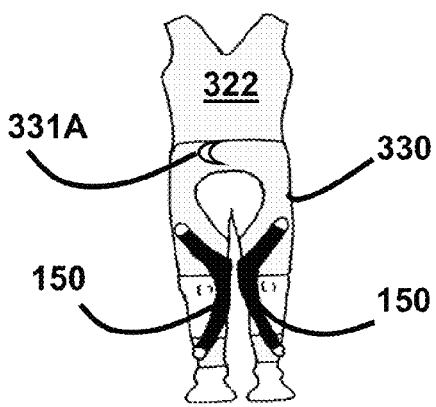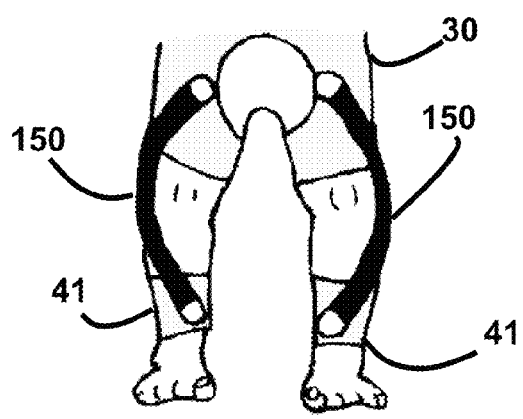
FIG. 24  FIG. 25
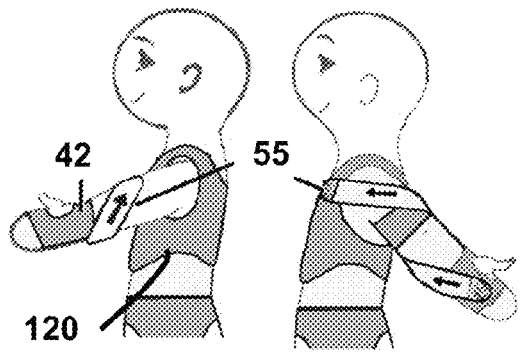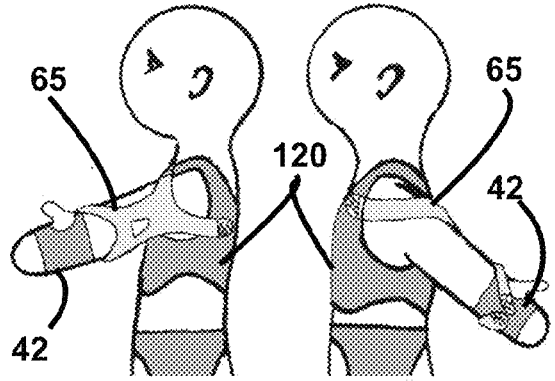
FIG. 26A  FIG. 26B  FIG. 27A  FIG. 27B

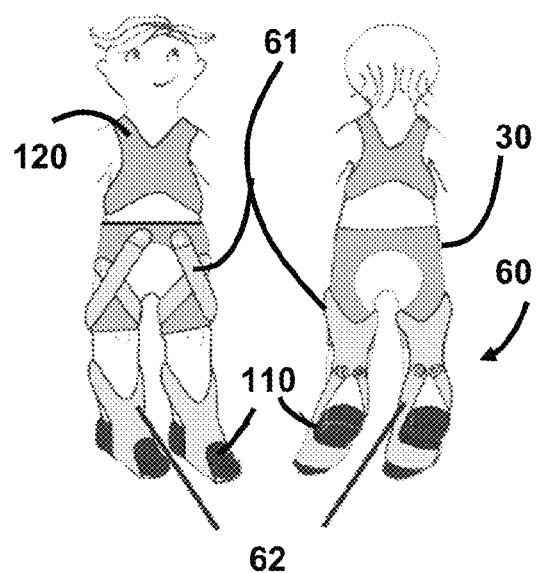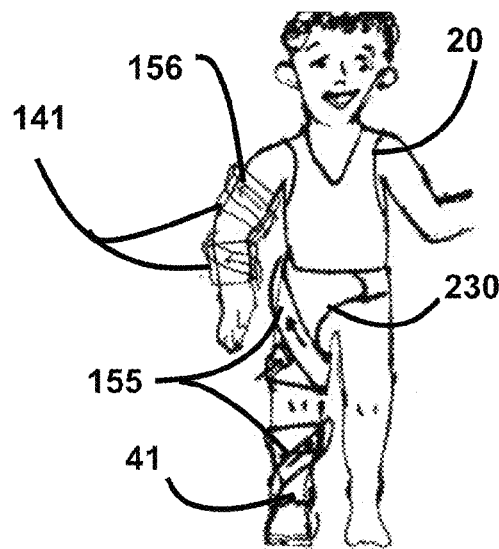
FIG. 28A  FIG. 28B  FIG. 29
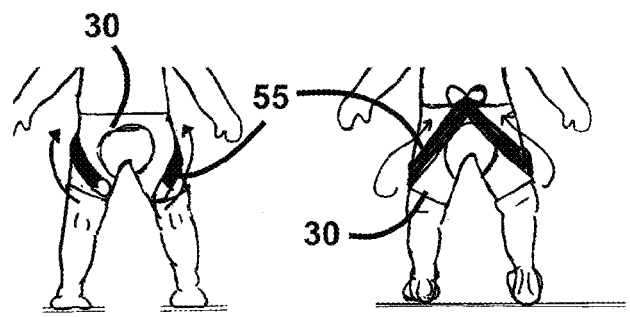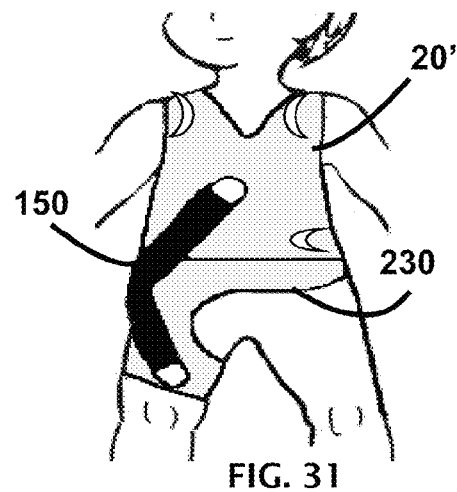
FIG. 30A  FIG. 30B  FIG. 31
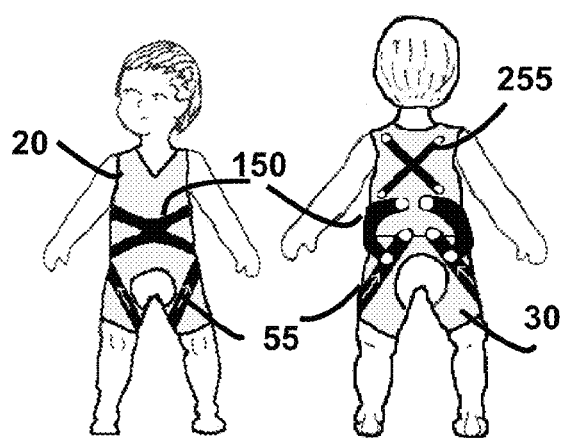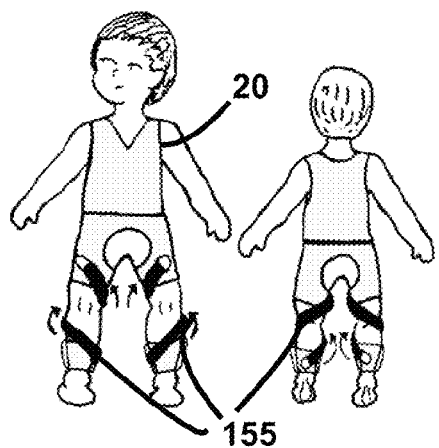
FIG. 32A  FIG. 32B  FIG. 33A  FIG. 33B

ELASTICIZED GARMENT AND STRAPPING SYSTEM TO AID IN BODY MOBILITY SUPPORT AND MAINTENANCE

BACKGROUND OF THE INVENTION

In general, the invention relates to attire and apparel that may be used in connection with: sensorimotor training and for purposes of functional static and dynamic stability and support of a mammalian body, in conjunction with skilled-services rendered by medical and veterinary physical and/or occupational therapists; bone density and muscle tone maintenance, especially within an environment where 'weightlessness' affects a body, as is experienced outside Earth's atmosphere where Earth's gravitational effects are less; for purposes of maintaining or enhancing athleticism/fitness whether for general strength training, muscle toning and body fitness and/or in connection with targeted athletic training for competitive performance; and various mechanical aids used to position topically-applied therapeutic devices such as hot-cold packs, structural splints of moldable plastically-deformable alloy such as are worn for sprains, weighted packs, an laser/LED therapy device, vibrators, electrical or acupressure point stimulation type unit(s).

More particularly, the invention is directed to a new modality to aid in issues of: body mobility, e.g., as an aid in sensorimotor training during and between physical and occupational therapy sessions (to address sensorimotor impairments and deficits, etc.) such as to restrict undesirable movement or promote corrective movement; truncal and limb support whether under static and dynamic conditions; bone density and muscle tone maintenance; improving postural alignment and stability; assist in building muscle strength, athletic training and performance; and so on, all as further disclosed. The unique system of elasticized upper- and lower-torso and limb garments, and elasticized pieces, each of which outlines a unique shape cut from an elasticized, foam-lined fabric that has been selected for its ability to remain stable on the skin surface, and to ventilate, allowing for skin and body temperature regulation. The garments may be worn directly on or next to the skin, or over a thin, close-fitting undergarment of cotton or other suitable lightweight material, and under regular attire, providing the wearer an outer flexible 'field' (or second skin) under which is a low- (or non-) slip inner surface. The outer 'external skin' functions as a stable field to which elongated elasticized pieces can be temporarily adhered in any configuration.

The garments preferably are cut from elasticized fabric to make optimum use of the variance in caliber of stiffness comparing the warp and weave in the fabric. FABRIFOAM® brand fabric (distributed by Applied Technologies, Inc.), for example, provides greater caliber of stiffness and is preferably aligned vertically for each of the torso garments, to aid in reducing side-to-side joint deviations. The greater caliber of extensibility (and reduces stiffness) is aligned horizontally in each garment, to facilitate fitting and comfort, and to allow for expansion of the woven fabric for the ventilating of body heat and moisture. As explained herein, the unique garment shapes, fitting and fastening mechanisms, and applications of the two-piece therapeutic garment system of the invention provides a powerful flexible tool (which can be distributed as a kit of components including garment shape and securing mechanism, elasticized straps, means for marking strap attachment sites, and instructional media) for physical and occupational therapists, and others who render veterinarian and human orthopedic and chiropractic care, to address issues of postural alignment, movement skill, joint stability, joint motion, and body balance.

Applicant's earlier attempts, dating from 1999 through 2001, are depicted as patterns in FIGS. 1, 2, 4, 5—with FIG. 3 illustrating the ill-fitting patterned pieces of FIGS. 1, 2A-2B on a young model, are included for background reference only. As one will appreciate, the new flexible upper- and lower-torso garments of the invention are distinguishable from applicant's earlier attempts as well as from conventional unitard-type garments, the traditional limb splints made of neoprene, elasticized cotton, or other materials, as injury support splints for shoulders, knees, ankles, elbows, and wrists using, for example, FABRIFOAM®, and the classic injury support elastic wrapping tape/ribbon known as 'ace bandages'. Furthermore, the invention is distinguishable from the CP rehab suit known as the Adeli Suit, developed in Russia for use by their cosmonauts, and since adapted for use in strength training for children with movement disorders, in that the Adeli Suit is a complex strengthening system of laces, buckled straps, and mounts, attached to a suit comprised of a short vest and shorts made of non-stretch fabric, for the application of elasticized Bungie®-type cords (for reference: www.adeli-suit.com). The precursor to the Adeli Suit was the Penguin loading suit.

As is well known, VELCRO® brand nylon fasteners consist of two mating NYLON components: hooks and loops (for reference, see www.velcro.com). The woven hook tape consists of tiny, flexible "hooks" which engage with a mating loop tape comprised of small, soft woven or knitted "loops." When pressed together, the resulting closure is adjustable and provides a secure releasable mechanism of fastening. To reopen the closure, it is simply peeled apart. VELCRO® hook and loop fasteners are detailed in U.S. Pat. No. 4,775,310, FIGS. 8-13, and U.S. Pat. No. 5,802,676, FIG. 6. For example, Velcro USA Inc. distributes many different types of hook and loop fasteners: Hook #65—lightweight, designed for maximum cycling (opening and closing); Hook #88—heavier weight hook tape; Loop #1000—napped tape (woven nylon loops that are "randomly disoriented" separately, after weaving); Loop #2000—an unnapped loop tape (woven nylon tape that is not napped) with a greater cycle life and less peel resistance than Loop #1000. By way of further background, C. L. Allen has patented an orthotic unitard-type "device made form a multi-directional stretchable spandex material" which may exhibit or have "flexible compression and stabilizing" aspects: U.S. Pat. No. 5,957,873 of 28 Sep. 1999; U.S. Pat. No. 5,782,790 of 21 Jul. 1998; and U.S. Pat. No. 6,086,551 of 11 Jul. 2000.

SUMMARY OF THE INVENTION

It is a primary object of the invention to provide a therapeutic garment system for use on a mammalian body, and associated method of donning, whereby the garments are adapted for donning and releasably securing in a close-fitting fashion so that a plurality of elasticized pieces may be releasably applied, utilizing fasteners, against an outwardly facing surface of at least one—and more often two—of the garments in an operative therapeutic configuration.

As can and will be appreciated, certain of the many unique features, as well as the further-unique combinations thereof, supported and contemplated hereby within the spirit and scope of this disclosure, may provide a variety of advantages. The advantages of the new features and combinations disclosed hereby will be appreciated, especially by providers of medical or veterinary services, by perusing the instant technical discussion, including drawings, claims, and abstract, in light of drawbacks to traditional therapies and devices identified throughout, or as may be uncovered. The unique garment shapes and strapping configuration opportunities provide versatility to accommodate a wide variety of objectives.

Briefly described, the garment system of the invention has at least one elasticized garment for donning around an area of a torso such as the upper-torso (top), lower-torso (bottom), or full-torso area. The system preferably also includes a second elasticized garment for donning and releasably securing in a close-fitting fashion around a portion of the body, other than that around which the first garment will (or has been) be donned. The second garment may be patterned for donning around an area of the torso other than that selected for the first garment (e.g., if the first garment is for upper-torso area, the second is for lower-torso area), or a 'limb' of the body such as an arm, a shoulder, a hand, a leg, a hip, a foot, or the head. A variety of limb garments are contemplated hereby, such as a shoulder wrap, an upper-arm cuff, an elbow cuff, a forearm-area cuff, a wrist wrap, a hand sleeve wrap, an upper-leg cuff, a knee cuff, a shin-calf area cuff, an ankle wrap, a foot wrap, and a cap for the head. In addition to an outwardly facing surface adapted for accepting releasable fasteners, each garment has an under-layer with an inwardly facing surface to resist slippage when donned. The inwardly facing surface may be worn in direct contact, next to the body's skin or over a snug, thin undergarment.

As one will appreciate, a wide variety of operative therapeutic configurations are available to one doming the components of a garment system of the invention, including those that address generally targeted objectives such as, by way of example: improve body posture by postural retraining (whether just mechanically, while the body is in a static/stationary mode, and/or mechanically and dynamically, when the body is in motion); improve balance control of the body; improve movement control of the body; assist in body neuromotor re-education; assist in skeletal modeling of the body; support an injured area of the body; promote movement of at least a part of the body for athletic performance enhancement; assist in maintaining muscle tone by applying elasticized resistance to movement of a part of the body when in an environment wherein an effect from a gravitational force (coined as 'weightlessness') is less than the gravitational effects experienced on Earth; assist in stabilizing a joint of the body; and assist in maintaining, in a positional relationship to the body, a topically-applied therapeutic device. Further, using applicant's unique core designs along with the information contained herein, skilled artisans may identify other objectives for which the garment system can be used, and establish associated therapeutic configurations, all of which are contemplated and covered, according to the invention.

While an objective may be determined during a rehab, treatment, training, or therapy session with a medical skilled-service provider, including physical, occupational, etc., therapists as well as other ancillary and primary health professionals rendering skilled services to a human or veterinary patient, it need not be. The objective to improve body posture may further comprise dynamic postural retraining; the objective to assist in maintaining muscle tone may further including assisting in maintaining bone density by applying elasticized joint compression. The topically-applied therapeutic device may be of any size and weight suitable for securing, locating, or attaching to the garment system utilizing the elasticized pieces and releasable fasteners including any of the following: thermally regulated (e.g., hot and/or cold) pack, a weighted pack for reducing osteoporosis, an anodyne laser therapy device, an anodyne light-emitting-diode (LED) therapy device, a structural splint of plastically-deformable/moldable alloy, a vibrator device, an electrical stimulation unit, an acupressure point stimulator, and a Chakra point stimulator.

Associated with the garment system of the invention, is a method for donning a therapeutic garment system on a mammalian body. The method includes: donning an elasticized garment comprising an under-layer having an inwardly facing surface to resist slippage while on the body, and releasably securing the garment in a close-fitting fashion around at least a portion of the body's torso; donning a second elasticized garment, comprising an under-layer having an inwardly facing surface to resist slippage while on the body, and releasably securing this second garment in a close-filling fashion around at least a second body portion other than that for the first garment; and releasably applying against an outwardly facing surface of each of the garments, a plurality of elasticized pieces in an operative therapeutic configuration.

Further distinguishing features of both the garment system and method of donning are numerous. One or more of the elasticized pieces may be generally linear-elongated in shape (e.g., strap 55, FIG. 13) or shaped in an at least partially split-strap configuration having at least first and second extensions (e.g., split-strap 50, FIG. 12, flex strap/split configurations 61, 62 FIG. 14, and 65, FIG. 15). For example (FIG. 12) an elasticized piece of a partially split-strap configuration may have first and second extensions (51A, 51B) opposite third and fourth extensions (52A, 52B), whereby the split-strap elasticized piece is adapted for application to at least one of the outwardly facing surfaces by utilizing at least one fasteners at each of an end of the first, second, third, and fourth extensions.

While it can be cut as a unitary garment (e.g., FIG. 6, 20), the upper-torso garment preferably comprises front and back panels (e.g., FIG. 7, 20') which are releasably secured at each of a shoulder area of the panels and at each of a right and left side of each panel. Likewise, while it may be of a unitary style (e.g., FIG. 8, 30), the lower-torso garment may comprise right-side and left-side panels: here, each panel includes a waistband portion having a first and second end, with each respective waistband portion interconnected with a thigh-wrap portion having a lower perimeter. One of the waistband ends of each panel is preferably adapted for releasably securing in the front of the body, and the other waistband end of each panel are adapted for releasably securing in the back (reference FIGS. 41, 42). The outwardly facing surface of each garment may comprise a woven fabric with the under-layer comprising a polyether-polyurethane foam lining. Likewise, each of the elasticized pieces may comprise a foam-lined woven fabric, an outer surface of which is also adapted for accepting said releasable fasteners.

Size-tailoring indicia is preferably included and extending along, in offset proximity to, at least a portion of a perimeter of the upper-torso garment such as a portion of the perimeter of the front and back panels, and at least a portion of a lower perimeter of the thigh-wraps of one or more lower-torso panel. Sizing of each garment may then be done after an initial donning, by trimming along one of the selected size-tailoring indicia for a comfortable, snug fit. Releasable fasteners may be any mechanism suitable for releasably securing elasticized pieces and compatible with the outwardly facing surface fabric selected, such as: an area having tiny flexible hooks for engagement with mating loop fabric (e.g., VELCRO® NYLON hook-type tabs, sections of VELCRO® taping or ribbon, etc.); an area comprising an array of snaps; an area comprising an array of D-rings; an area comprising an array of small buckles (especially, quick-release snap buckles often found on sporting gear); and an area comprising an array of hook-and-eye enclosures (e.g., as used on clothing). A plurality of position markers adapted for application to any of the outwardly facing surfaces may be included for marking a location for re-donning a torso area or limb garment once initially fit to the body in a close-fitting fashion. Also position markers may be included and adapted for marking a configuration of elasticized pieces, once determined, for re-application.

BRIEF DESCRIPTION OF THE DRAWINGS

For purposes of illustrating the innovative nature plus the flexibility of design and versatility of preferred and alternative garment systems and associated donning technique(s), supported and disclosed hereby, the invention will be better appreciated by reviewing accompanying drawings (in which like numerals designate like parts). One will appreciate the many features that distinguish the instant invention from traditional therapies and applicant's own, earlier design attempts. The drawings have been included to communicate features of the innovative structures and associated donning technique of the invention as well as to demonstrate the unique approach taken by the applicant by way of example, only, and are in no way intended to unduly limit the disclosure hereof.

FIGS. 1-5 depict applicant's published designs, dating from 1999 through 2001, included herewith for purposes of illustrating applicant's earlier attempts: FIG. 1 is a top plan view of a pattern for a unitary top with wing sleeves; FIG. 2A is a top plan view of a pattern for a pant; FIGS. 2B and 2C are, respectively, front and back plan views of the pant in FIG. 2A, as assembled. FIG. 3 is of a young model wearing the top 10 of FIG. 1 and the pant of FIGS. 2A-2C. FIGS. 4 and 5 are top plan views of, respectively, a pattern for a pant having two thigh wraps coined by applicant as a "hipster" and a pattern for a pant having one thigh wrap coined by applicant as a "unihipster."

FIG. 6 is a top plan view representing an upper-torso garment 20 of the invention having been cut as a unitary piece.

FIG. 7 is a front plan view of an upper-torso garment 20' preferably comprised of a front panel 22' and a back panel (behind and out of view, here) secured with fasteners 29A-B, and 28A-B.

FIG. 8 is a top plan view representing a lower-torso garment 30 of the invention having been cut as a unitary piece.

FIG. 9 is a top plan view representing a limb garment 41 of the invention designed for donning around a part of the leg or arm.

FIG. 10 is top plan view representing a limb garment 42 of the invention designed to be donned around a hand and wrist.

FIG. 11 is a top plan view representing a limb garment 45 of the invention designed to be donned atop a human head such as is depicted in FIGS. 17A-17B.

FIGS. 12-15 are top plan views representing various uniquely shaped elasticized strapping pieces of the invention; respectively, a double split-strap configuration 50 in FIG. 12, a generally elongated strap 55 in FIG. 13, a two piece split-strap configuration in FIG. 14, and a double split-strap 65 in FIG. 15.

FIGS. 16A-16B depict a young human model 100 to which a strapping configuration has been applied, FIG. 16B, to upper-torso and lower-torso garments.

FIGS. 17A-17B depict a young human model to which a strapping configuration has been applied to an alternative 'short' upper-torso garment, a lower-torso garment, and a limb (cap) garment 45.

FIGS. 18A-18B depict a young model to which a strapping configuration has been applied (two split-straps 150) to upper-torso and lower-torso garments.

FIGS. 19A-19B depict a young model to which a strapping configuration has been applied (two split-straps 50) to short upper-torso and lower-torso garments.

FIGS. 20A-20C depict a human leg to which a strapping configuration has been applied (elongated strap 75) to two limb garments.

FIGS. 21A-21C depict a human leg to which a strapping configuration has been applied (elongated straps 95A, 95B) to two limb garments, here, two similar leg cuffs 91. FIG. 21A is a lateral (i.e., side) view with no strapping yet applied, FIG. 21B is an anterior (i.e., front) view; FIG. 21C is a posterior (i.e., back) view.

FIG. 22A is an anterior view and FIG. 22B is a posterior view with split-strap 150 configurations applied.

FIG. 23 is a lateral view of a split-strap 50 applied to a leg cuff and the lower-torso garment depicted.

FIGS. 24 and 25 are both anterior (i.e., front) views with split-strap 150 configurations applied to each leg cuff and the lower-torso garment depicted.

FIGS. 26A-26B are lateral views of an elongated strap 55 applied to a hand-wrist cuff and short upper-torso garment depicted.

FIGS. 27A-27B are lateral views of a split-strap 65 applied to a hand-wrist cuff and short upper-torso garment.

FIG. 28A is an anterior (i.e., front) view and FIG. 28B is a posterior (i.e., back) view with split-strap 61/62 configurations applied to each foot 'sock'/cuff 110 and the lower-torso garment depicted.

FIG. 29 depicts a human model to which a strapping configuration has been applied (elongated strap 156) to two limb garments, similar arm cuffs 141, and a strapping configuration has been applied (elongated strap 155) to leg cuff 41 and an alternative lower-torso garment 230 (illustrated with only one thigh-wrap).

FIG. 30A is an anterior view and FIG. 30B is a posterior view with elongated straps 55 applied to the garments depicted.

FIG. 31 is an anterior view of a split-strap 150 applied to the upper-torso and lower-torso garments depicted.

FIG. 32A is an anterior view and FIG. 32B is a posterior view with a configuration of elongated straps 55, split-straps 150, and shorter elongated straps 255 applied to the upper-torso and lower-torso garments depicted.

FIG. 33A is an anterior view and FIG. 33B is a posterior view illustrating yet another unique configuration of elongated straps 155.

FIG. 34 is an anterior view of upper-torso garment 20' undergoing a sizing; FIG. 35 depicts right-side of front panel 22' undergoing trimming; FIG. 36 is a lateral (i.e., side) view illustrating the securing of left-side of a back panel using banana-shaped fastener 28B, to front panel 22'; FIG. 37 is an anterior view illustrating use of position markers (such as dots applied, as shown at 27') on the outwardly facing surface of the upper-torso garment depicted; FIG. 38 is an anterior view illustrating the fastening of the right-side of a back panel using banana-shaped fastener 28A to fit upper-torso garment in a close-fitting fashion; FIG. 39 depicts a human model to which a lower-torso garment is being donned; FIG. 40 depicts the human model of FIG. 39 to which waistband portion has been secured with fastener 31, thigh-wrap portion 34 has been donned, and thigh-wrap portion 33 is being wrapped; FIG. 41 is an anterior view illustrating the lower-torso garmented depicted in FIGS. 39-40, donned in a close-fitting fashion, ready for applying elasticized strapping configuration(s) such as those shown in FIGS. 17A-B, 18A-B, 19A-B, 25, 28A-B, 30A-B, 32A-B, 33A-B; and FIG. 42 is a posterior view of an adult model with a lower-torso garment donned in a close-fitting fashion.

DETAILED DESCRIPTION OF EMBODIMENTS DEPICTED IN THE DRAWINGS

Figure 34:
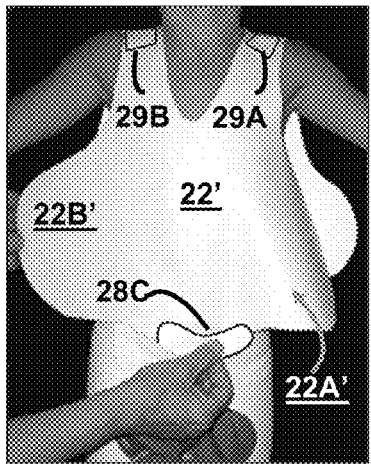
FIGS. 34-42 illustrate examples of donning techniques according to the invention.

In connection with discussing FIGS. 6 through 33, occasional reference will be made to FIG. 34 through 42 detailing core and further unique and distinguishing features, of a method of donning garments according to the invention. Feature details of a method for donning a therapeutic garment system on a mammalian body according to the invention, are readily ascertainable by reviewing the accompanying figures and supporting text such that further visual depiction, by way of a formal flow diagram, is unnecessary. As used throughout this technical disclosure, "therapeutic" includes curative; healing (soothing); restorative; corrective; medicinal; salubrious (health-giving); remedial; and/or beneficial, whether in connection with normal or enhanced body functioning (such as in the case for athletic performance) or contributing to or for the cure of any malady. "Animal", if referenced herein, includes any multicellular organism having a body that can move voluntarily and actively acquire food and digest it internally, including human beings and other mammals. Fabric as used herein includes cloth and any other flexible material made, woven, knitted, intermingled, etc., natural or synthetic fibers and/or filaments, whether thermal energy is applied to produce the fabric, and whether the fibers or filaments are made, into threads, cording, yarns, etc., prior to fabricating the fabric. VELCRO® brand tape, tabs, sheeting, etc., and FABRIFOAM®, are all considered fabrics for purposes of this technical discussion.

By way of example only, materials of interest for fabricating garments and elasticized pieces of the invention for clinical, training, performance, and research purposes, include the material showcased and identified herein as FABRIFOAM® manufactured by Applied Technologies, Inc. More-particularly, of interest are the FABRIFOAM® brand named products known as NuStimWrap™, MediWrap™, and ProWrap™, see www.fabrifoam.com for further reference. These multi-layer elasticized fabric materials provide comfortable bidirectional elasticity: they are foam-lined, made by bonding polyether-polyurethane foam, an aqueous-based elastomeric urethane, onto a fabric comprised of NYLON and SPANDEX, neither element of which contains LATEX® rubber, and provides the properties of variable elasticity (whereby the warp is stiffer than the weave) "breatheability", allowing body heat and perspiration to ventilate through the material, and slip-resistance on the body. Percentage amounts of components in any of the FABRIFOAM® fabrics vary depending on specific engineered material design. The foam component will vary in thickness depending on specific use intended for the composite material.

Turning to FIG. 6, upper-torso garment 20 may be cut as a unitary piece from a multi-layer fabric, such as a foam-lined, elasticized material. The front panel 22 has a right-side 22A and left-side 22B and an integral back panel 24, also with a right-side 24A and left-side 24B: 22A to mate with 24A and 22B to mate with 24B—for securing garment 20 around the trunk of a wearer. Sizing indicia of the front panel is labeled 22C-t (toddler cut line), 22D-yp (young-preschooler cut line), and 26C along the perimeter of the arms—also extends to back panel 24. Cut-here indicia may also be included on the back panel 24C. An aperture 21 is provided for donning the garment over the wearer's head and neck. Options for producing "cut-here" markings include: perforations (partially or fully-through fabric to aid in removing separating), silk-screen/stenciling, printing, heat or otherwise embossing, and any other suitable marking. Once a garment of appropriate body-weight-related size is selected (garments may accommodate a range of body-weights), an attending clinician sizes or fits a garment(s) 20, 22', 30 to the wearer by using handy "cut/trim here" markings embossed on the garment.

The preferred alternative upper-torso garment 20' in FIG. 7 has a front panel 22' and a back panel (behind and out of view, here) secured with shoulder area fasteners 29A, 29B, with neck opening 21' therebetween, and 'banana shaped' fasteners 28A, 28B to releasably secure, respectively, sides 22A' and 22B'. Trim lines 26C' and 22C' are illustrated along, and offset, the perimeter of the 'arm hole' area and the lower perimeter of the front panel 22'. As mentioned, the releasable fasteners (areas 29A, 29B and 28A, 28B) may be any mechanism suitable for releasably securing elasticized pieces and compatible with the outwardly facing surface fabric selected, such as: an area having tiny flexible hooks for engagement with mating loop fabric (e.g., VELCRO® NYLON hook-type tabs, sections of VELCRO® taping or ribbon, etc.); an area comprising an array of snaps; an area comprising an array of D-rings; an area comprising an array of small buckles (especially, quick-release snap buckles often found on sporting gear); and an area comprising an array of hook-and-eye enclosures (e.g., as used on clothing).

FIG. 8 is a top plan view representing a lower-torso garment 30 of the invention having been cut as a unitary piece from preferably a multi-layer, i.e., foam-lined, elasticized material. It has a waistband section 32 that wraps around a wearer's waist such that anterior side-portions 32A and 32B overlap so they can be releasably secured at 31 with, for example, a hook-type tab. Left and right thigh wrap sections, 33 and 34, respectively, have side-portion flaps 33A and 33B on the left side thigh-wrap 33 side, and 34A and 34B on the right side thigh-wrap 34, each pair overlap when wrapped around the wearer's thigh (see also, FIGS. 41, 42). Each thigh wrap section is either secured in place with, for example, a high-tension, banana shaped, hook-type tab 38, 39, or sewn into a conical-cylinder-shaped cuff to fit the wearer. Garment 30 is preferably worn next to the skin and under all clothing, with an aperture on the front and back sides of the body that exposes the perianal area for the purpose of allowing toileting without soiling the garment, and without requiring that the garment, or any component of it, be doffed. A waistband portion of lower-torso garment 30 may be split (dashed line at 23C) into two sections to form a right and left panel of the garment, which are secured in front and back (see also FIGS. 41, 42). Sizing-trim indicia are shown as dashed lines 36A, 36B along the lower perimeter of each thigh wrap 33, 34.

The limb garment 41 in FIG. 9 is shaped for donning around a part of the leg or arm, with an inwardly facing slip-resistant surface next to the skin. This garment may be positioned anywhere along the leg or arm (e.g., just below the calf muscle or in a host of other positions as illustrated herein), so that end portions 41A and 41B may overlap for securing in place with suitable releasable fastener 40, such as a high-tension hook-type tab. The unique shape of the limb garment 42 of FIG. 10 is shaped for donning around a hand and wrist, such as depicted generally in FIGS. 26A-26B and 27A-27B. The garment 42 may be applied over the thumb, first, foam-side next to the skin, wrapping the remaining flaps around the hand (42C and 42D) and wrist (42E and 42F), leaving all five digits exposed. The flaps are then secured with high-tension hook-type tabs, of which one may be embedded into the foam side of the material of section 42D. After overlapping section 42D onto 42C on the dorsum of the hand, the embedded hook tab attaches to the exterior surface of flap 42C. Alternatively, garment 42 may be fitted to the wearer and sewn rather than tabbed, such that the wearer would pull the sleeve onto the extremity. Another limb garment 45 of FIG. 11 is designed to be donned atop a human head such as is depicted in FIGS. 17A-17B, to provide gentle compression.

The uniquely shaped elasticized strapping pieces in FIGS. 12-15 include a 'double' split-strap configuration 50 in FIG. 12, a generally elongated strap 55 in FIG. 13, a two piece split-strap configuration in FIG. 14, and a double split-strap 65 in FIG. 15. The split-strap 50 may be cut from a foam-lined, elasticized fabric exhibiting a higher caliber of stiffness than that which is inherent in the preferred fabric used for manufacturing the torso and limb garments. Split Strap 50 (as well as split-strap 65) is bifurcated on both ends, designated as end sections 51 and 52, each partially split forming two projections/extensions of fabric, 51A and 51B on the proximal end 51 of the piece, and extensions 52A and 52B on the distal end 52, each of which attaches to the underlying garment with a releasable enclosure such as a very high-tension hook-type tab. Here, the proximal extensions 51A, 51B are shorter in length compared with the distal straps, allowing optimum application of the proximal end split-strap to the shoulder areas of the short upper-torso garment 120, with the distal end split-strap(s) 52A, 52B around the pelvis and thigh sections of lower-torso garment 30. The curvilinear cut at a 'base' interposed between each bifurcated end 51A, B and 52A, B is designed to add strength and application versatility to the strapping system using this component of the invention. The two-piece strap 60 in FIG. 14 has a section 61 with extensions 61A, 61B and the bifurcated split-strap 65 of FIG. 15 has extension pairs: 65A-B, and 65C-D. Once again, one pair of extensions is shorter than the opposite pair of extensions.

Split straps such is shown at 50, 60, and 65 of FIGS. 13-15, are preferably fabricated to make optimum use of the variance in caliber of stiffness comparing the warp and weave in the selected elasticized fabric. The greater caliber of stiffness is aligned longitudinally for each split-strap. The longitudinal alignment of the warp in the material, and the width of a center panel/region 53, combined to maximize both the potential joint compression and the resistance to joint motions applied by the entire split-strap 50. The trapezoid-shaped (or other shape) 'window' in central region 53 or of split-strap 65 at 65E, serves as a vent that allows for a measure of body heat release through the strap, or for accommodating knee or elbow positioning, or locating a therapeutic device, and so on.

As mentioned, a wide variety of operative therapeutic configurations are available to one donning the components of a garment system of the invention, including those that address generally targeted objectives such as, by way of example those detailed further, below:

(a) For postural retraining for problems related to muscle weakness, ligament laxity, hypotonia, osteoporosis, upper motor neuron syndrome following stroke, traumatic brain injury: An orthotic undergarment and elasticized strapping system is tailored to mechanically and dynamically improve posture, providing the client with the training effect of the sensory experience, and with an orthotic adjunct to a specific strengthening exercise program:

Flexible kyphosis—i.e. manually correctable: straps are applied to straighten the upper spine and bring the shoulders back. This application often requires counter support with crossed straps over the abdominals.

Flexible lumbar lordosis—i.e. manually correctable: straps are used to help the abdominals to flex the lower spine, and to extend the hips, with the result of flattening the lumbar spine.

Flexible scoliosis—i.e. manually correctable: straps are applied to reduce the magnitude of postural convexities (b) For balancing and movement control deficits due to sensory integration deficits, and to injury to the cerebellum (ataxia), the vestibular system (dizziness), or the extrapyramidal nervous system (athetosis, dystonia):

Staggering gait and lack of postural stability and hand control due to ataxia, that reduce with manual compression through the trunk, shoulder, and/or hip joints: the garments, alone, or with straps, use vertical compression through the trunk and hip joints and circumferential compression around the trunk and thighs to improve balance and reduce staggering gait by increasing proprioceptive and tactile sensory input and reducing load-bearing joint deviations.

Postural insecurity, difficulty organizing bilateral, synchronous movements against gravity, fear of rapid acceleration and deceleration, related to sensory integration: the garments, alone or with limb cuffs and a strapping system, use circumferential compression around the trunk and thighs to improve balance and to provide increased body awareness by enhancing proprioceptive and tactile sensory input.

Involuntary trunk and limb movements that reduce with manual correction or compression, as occur in the presence of athetosis or dystonia: the garments, limb cuffs, and selected straps are applied to reduce the magnitude of involuntary movements.

(c) For neuromotor re-education and skeletal modeling (determined by client's age and consistency of use of the system) for problems of gait pattern and efficiency (ambulation), arm and hand use, and muscle recruitment due to injury to the areas of the central nervous system that control movement and walking (cerebral palsy, stroke, traumatic brain injury):

In-toed or out-toed gait deviations due to a problem of muscle recruitment or imbalance of power at the hip or due to torsional deviation in the femur: straps are applied to gently rotate the thigh as needed to improve knee joint alignment and function, and to improve the recruitment of muscles that cross the hip joint in the swing phase of gait. The client experiences the sensation of more kinesiologically appropriate movement throughout the day In-toed or out-toed gait deviations due to a problem of ligament laxity or muscle imbalance at the knee joint or torsional deviation in the leg bones: straps are used to gently rotate the leg unit as needed to improve foot alignment and function in standing and gait.

Scissoring gait, manually correctable: straps are used to reduce hip adduction and to keep the legs apart.

"Crouch" posture and gait, manually correctable: straps can be used to reduce trunk, hip, and knee flexion while appropriate ankle-foot orthoses resist forward tilt of the legs at the ankles.

"Posturing" of one or both upper extremities in a spastic pattern of manually-correctable shoulder protraction and elevation, elbow and wrist flexion, and forearm pronation: straps can be used to realign the shoulder on the trunk, to correct rotation of the arm at the shoulder, to extend the elbow, and to supinate the pronated forearm.

According to the invention, the garments system and technique for donning, employ the principle of applying prolonged, low-load (i.e. gentle) forces to the musculoskeletal system in order to attempt to effect changes in muscle recruitment strategies, and, with full-time use, in muscle physiology and bone geometry over thousands of movements per day. A provider/practitioner might use any combination of tension-generating force vectors and magnitudes—afforded by an array of elasticized elongated pieces attached to garments and cuffs with removable fasteners—to design a system of straps that persistently and gently manipulates the wearer's musculoskeletal system for as long as he/she wears it—and in some cases, for hours or days after removing it. Strapping application(s), using the unique elasticized pieces according to the invention, may be configured to replicate gentle, non-forced manual correction that a clinician can apply to a wearer's posture, balance, or limb motion. The system is preferably introduced to a wearer in small stages over time, allowing gradual adjustment to any new demands of each strap, and allowing caretakers, who will be re-donning the garments and re-applying the strapping configuration designed by a provider, to learn to apply the system correctly in stages.

A wearer gains experience—and training potential—of prolonged therapeutic "handling" throughout the day, every day, as s/he undertakes routine activities using improvements in posture and joint alignment induced by the unique invention, and while recruiting muscles at more normal lengths than would occur in the presence of postural defects. A properly fitted garment system provides a wearer a breathable, "second skin" over his/her trunk and selected limb segments, while also providing vertical stiffness to reinforce the wearer's stability, and lateral flexibility to provide mild compression and a comfortable fit. Providers who fit the garments can undertake a full musculoskeletal assessment of the potential wearer prior to designing a strapping configuration, in order to identify problems of skeletal geometry versus muscle imbalance or joint laxity, and to exercise proper caution and restraint in seeking correction of pathomechanical and pathokinesiological function. Following are examples of a few of the many alternative configurations.

FIGS. 16A-16B depict a young human model 100 to which a strapping configuration has been applied for paraspinal extension, split-strap 150, FIG. 16B, to upper-torso 20 and lower-torso garments 30. FIGS. 17A-17B depict a strapping configuration applied, anterior and posterior split-straps 50 with straight straps 55 interconnecting the compression cap 45, for ataxia, neck muscle toning, resistance to all trunk and hip motion(s), to an alternative 'short' upper-torso garment 120, a lower-torso garment 30. FIGS. 18A-18B depict a strapping configuration applied, (i.e., two lateral split-straps 150) to a front 22' and back 24' panel of the upper-torso garment and a lower-torso garment 30 for providing trunk/hip compression. FIGS. 19A-19B depict a strapping configuration applied (i.e., two lateral split-straps 50) to short upper-torso 120 and lower-torso 30 garments.

FIGS. 20A-20C depict a human leg to which a strapping configuration has been applied (elongated strap 75) to two limb garments: leg/medial cuff 41 and foot 'sock'/cuff 71, each of which is also shown in top plan views labeled FIG. 20A, 20B. The strapping configuration depicted in FIGS. 21A-21C (elongated straps 95A, 95B) to two limb garments, here, two similar leg cuffs 91, operates as a knee hyper wrap. FIG. 21A is a lateral view with no strapping yet applied, FIG. 21B is an anterior view and FIG. 21C is a posterior view with straps 95A, 95B applied with releasable fasteners. FIG. 22A is an anterior view and FIG. 22B is a posterior view with split-strap 150 configurations applied to each leg cuff 41 and adult-sized lower-torso garment 330, for knee hyperextension and to facility knee flexion. FIG. 23 is a lateral view of a split-strap 50 applied to a leg cuff 41 and adult-sized lower-torso garment 330 to facilitate knee extension. FIGS. 24 and 25 are both anterior views with split-strap 150 configurations applied to each leg cuff and a lower-torso garment (330, FIG. 24 and 30 FIG. 45) releasably fastened in front with tab 331A; an adult-sized upper-torso garment 322 is shown, for reference in FIG. 24. Configuration in FIG. 24 is for genu valgum due to ligament laxity and that depicted in FIG. 25 is for genu varum due to ligament laxity.

FIGS. 26A-26B are lateral views of an elongated strap 55 applied to a hand-wrist cuff 42 and short upper-torso garment 120: FIG. 26A is of the back of the arm, FIG. 26B is of the inside of the arm, to illustrate strapping configuration, where elongated strap 55 is applied to resist extension at the shoulder, elbow, and wrist, and shoulder lateral rotation. FIGS. 27A-27B are lateral views of a split-strap 65 applied to a hand-wrist cuff 42 and short upper-torso garment 120: FIG. 27A is of the back of the arm, FIG. 27B is of the inside of the arm to help illustrate strapping configuration, where the flex split-strap 65 is applied to resist shoulder flexion and extension, and elbow and wrist flexion.

FIG. 28A is an anterior view and FIG. 28B is a posterior view with split-strap 61/62 configurations applied to each foot 'sock'/cuff 110 and lower-torso garment 30 to apply resistance to hip and knee extension and ankle plantarflexion. Also shown is the short upper-torso garment 120. FIG. 29 depicts a strapping configuration applied (elongated strap 156) to two limb garments, similar arm cuffs labeled 141, and a strapping configuration applied (elongated strap 155) to leg cuff 41 and an alternative lower-torso garment 230 (illustrated with only one thigh-wrap). FIG. 30A is an anterior view and FIG. 30B a posterior view with elongated straps 55 applied to an upper-torso garment and lower-torso garment 30, to facilitate hip extension with lateral rotation. FIG. 31 is an anterior view of a split-strap 150 unilaterally applied to upper-torso garment 20' and lower-torso garment 230 to increase hip abduction and stability and to reduce scissor gait. FIG. 32A is an anterior view and FIG. 32B a posterior view with a configuration of elongated straps 55, split-straps 150, and shorter elongated straps 255 applied to upper-torso garment 20 and lower-torso garment 30 for muscle dominance issues—to diminish recruitment of dorsal trunk, neck, and lower extremity musculature by helping to shift the anteriorly displaced weight line. FIG. 33A is an anterior view and FIG. 33B is posterior view illustrating yet another configuration comprising elongated straps 155 applied to each of the limb cuffs and lower-torso garment depicted to reduce excessive medial leg rotation.

Figure 35:
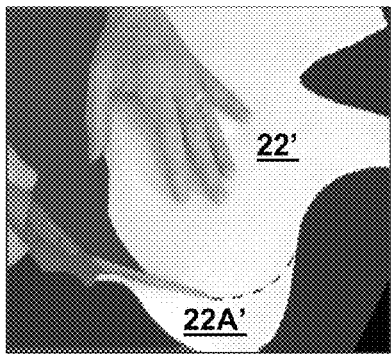
Figure 36:
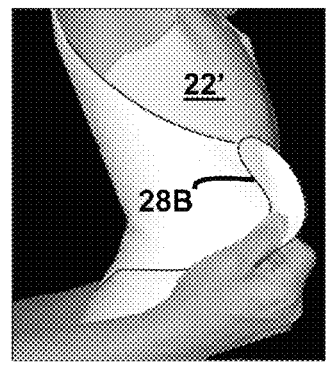
Figure 37:
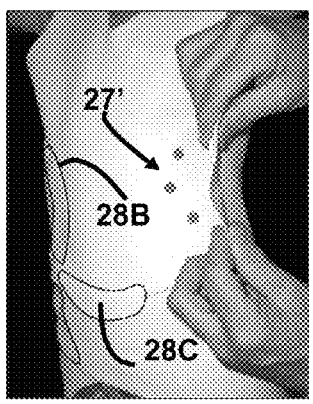
Figure 38:
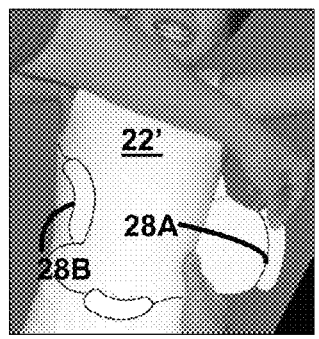
Figure 39:
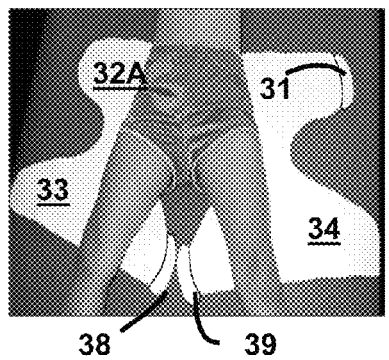
Figure 40:
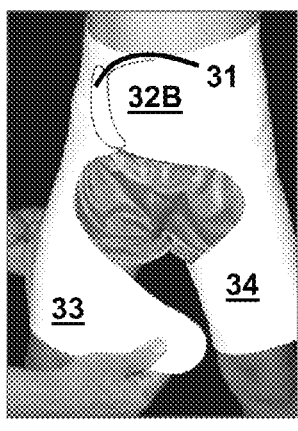
Figure 41:
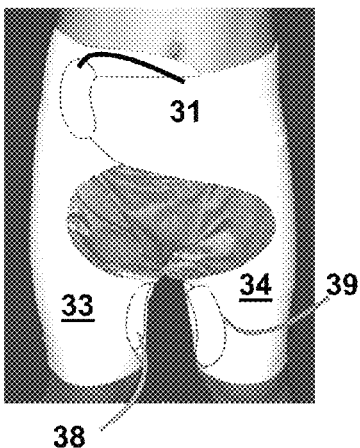

FIGS. 34-42 illustrate examples of donning techniques according to the invention: FIG. 34 is an anterior view of upper-torso garment 20' undergoing a sizing; FIG. 35 depicts right-side of front panel 22' undergoing trimming; FIG. 36 is a lateral (i.e., side) view illustrating the securing of left-side of a back panel using banana-shaped fastener 28B, to front panel 22'; FIG. 37 is an anterior view illustrating use of position markers (such as dots applied, as shown at 27') on the outwardly facing surface of the upper-torso garment depicted; FIG. 38 is an anterior view illustrating the fastening of the right-side of a back panel using banana-shaped fastener 28A to fit upper-torso garment in a close-fitting fashion; FIG. 39 depicts a human model to which a lower-torso garment is being donned; FIG. 40 depicts the human model of FIG. 39 to which waistband portion has been secured with fastener 31, thigh-wrap portion 34 has been donned, and thigh-wrap portion 33 is being wrapped; FIG. 41 is an anterior view illustrating the lower-torso garmented depicted in FIGS. 39-40, donned in a close-fitting fashion, ready for applying elasticized strapping configuration(s) such as those shown in FIGS.

Figure 42:
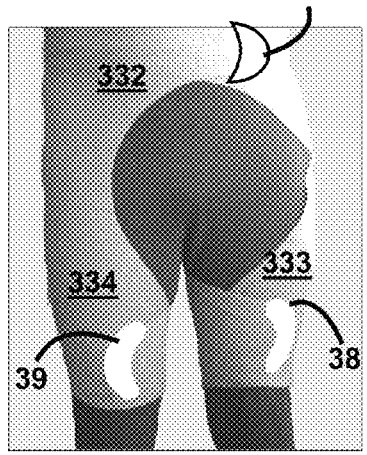

17A-B, 18A-B, 19A-B, 25, 28A-B, 30A-B, 32A-B, 33A-B; and FIG. 42 is a posterior view of an adult model with a lower-torso garment donned in a close-fitting fashion, ready for accepting strapping configuration(s).

While certain representative embodiments and details have been shown for the purpose of illustrating the invention, those skilled in the art will readily appreciate that various modifications, whether specifically or expressly identified herein, may be made to any of the representative embodiments without departing from the novel teachings or scope of this technical disclosure. Accordingly, all such modifications are contemplated and intended to be included within the scope of the claims. Although the commonly employed preamble phrase "comprising the steps of" may be used herein in a method claim, applicants do not intend to invoke 35 U.S.C. §112 ¶6. Furthermore, in any claim that is filed herewith or hereafter, any means-plus-function clauses used, or later found to be present, are intended to cover at least all structure(s) described herein as performing the recited function and not only structural equivalents but also equivalent structures.

What is claimed is:

1. A therapeutic garment system for use on a mammalian body, comprising:
    elasticized wrap-around first and second unitary style garments for donning and releasably securing in a close-fitting fashion at generally different areas of the body;
    each of said unitary style garments comprising an outwardly facing surface a substantial portion of which is adapted for accepting an area of releasable fasteners, and an under-layer having an inwardly facing surface to resist slippage when donned; and
    first and second separate elasticized pieces, each of said separate pieces comprising at least one of said areas of releasable fasteners for application of said piece onto said portion of said outwardly racing surfaces;
    wherein:
        said area of releasable fasteners of said first elasticized piece releasably applied against said portion of said outwardly facing surface of said first and second garment, interconnects said first elasticized piece with said first and second garments in an operative therapeutic configuration; and
        said second elasticized piece adapted to be releasably applied against said portion of said outwardly facing surface of either said first garment, said second garment, or both said first and second garment.

2. The garment system of claim 1 wherein said operative therapeutic configuration addresses an objective selected from the group consisting of: improve body posture by postural retraining; improve balance control of the body; improve movement control of the body; assist in body neuromotor re-education; assist in skeletal modeling of the body; support an injured area of the body; promote movement of at least a part of the body for athletic performance enhancement; assist in maintaining muscle tone by applying elasticized resistance to movement of a part of the body when in an environment wherein an effect from a gravitational force is less than the gravitational effects experienced on Earth; assist in stabilizing a joint of the body; and assist in maintaining, in a positional relationship to the body, a topically-applied therapeutic device.

3. The garment system of claim 1 wherein:
    said operative therapeutic configuration addresses an objective selected from the group consisting of: improve body posture by postural retraining; improve balance control of the body; improve movement control of the body; assist in body neuromotor re-education; assist in skeletal modeling of the body; support an injured area of the body; promote movement of at least a part of the body for athletic performance enhancement; assist in maintaining muscle tone by applying elasticized resistance to movement of a part of the body when in an environment wherein an effect from a gravitational force is less than the gravitational effects experienced on Earth; assist in stabilizing a joint of the body; and assist in maintaining, in a positional relationship to the body, a topically-applied therapeutic device; and
    said objective is determined during a session with a medical skilled-service provider; said objective to improve body posture further comprises dynamic postural retraining; said objective to assist in maintaining muscle tone further comprises assist in maintaining bone density by applying elasticized joint compression; and said topically-applied therapeutic device comprises a device selected from the group consisting of a thermally regulated pack, a weighted pack for reducing osteoporosis, an anodyne laser therapy device, an anodyne light-emitting-diode therapy device, a structural splint of plastically-moldable alloy, a vibrator device, an electrical stimulation unit, an acupressure point stimulator, and a Chakra point stimulator.

4. The garment system of claim 1 wherein: said first garment is donned around an upper-torso of the body by pulling said first garment over and around said upper-torso; and said second garment is donned around said different area of the body by wrapping said second garment around a portion of a limb of the body selected from the group consisting of an arm, a shoulder, a hand, a leg, a hip, a foot, and a head.

5. A garment system for use on a mammalian body, comprising:
    elasticized wrap-around first and second garments for donning and releasably securing in a close-fitting fashion at generally different areas of the body;
    each of said garments comprising an outwardly facing surface at least a portion of which is adapted for accepting an area of releasable fasteners, and an under-layer having an inwardly facing surface to resist slippage when donned;
    first and second separate elasticized pieces, each of said separate pieces comprising at least one of said areas of releasable fasteners for application of said piece onto any said portion of said outwardly facing surfaces;
    wherein said area of releasable fasteners of said first elasticized piece releasably applied against said portion of said outwardly facing surface of said first and second garment, interconnects said first elasticized piece with said first and second garments in an operative therapeutic configuration;
    said second elasticized piece adapted to be releasably applied against any said portion of said outwardly facing surface of either said first garment, said second garment, or both said first and second garment; and
    wherein: said second garment is a lower-torso garment and further comprises right-side and left-side panels; each said panel comprises a waistband portion having a first and second end, said waistband portion interconnected with a thigh-wrap portion having a lower perimeter, with size-tailoring indicia extending along, in proximity and offset, at least a portion of said lower perimeter; and said first waistband ends are adapted to be releasably secured in the body front, and said second waistband ends are adapted to be releasably secured in the body back.

6. A garment system for use on a mammalian body, comprising:
- elasticized wrap-around first and second garments for donning and releasably securing in a close-fitting fashion at generally different areas of the body;
- each of said garments comprising an outwardly facing surface at least a portion of which is adapted for accepting an area of releasable fasteners, and an under-layer having an inwardly facing surface to resist slippage when donned;
- first and second separate elasticized pieces, each of said separate pieces comprising at least one of said areas of releasable fasteners for application of said piece onto said portion of said outwardly facing surfaces;
- wherein said area of releasable fasteners of said first elasticized piece releasably applied against said portion of said outwardly facing surface of said first and second garment, interconnects said first elasticized piece with said first and second garments in an operative therapeutic configuration; and
- a plurality of position markers adapted for application to any of said outwardly facing surfaces for marking a location for re-donning said respective garment once initially fit to the body in said close-fitting fashion; said position markers further adapted for marking said configuration of said elasticized pieces for re-application; and wherein said area of releasable fasteners of second said second elasticized piece is releasably applied against said portion of said outwardly facing surface of each said first and second garments, interconnecting said second elasticized piece with said garments.

7. A garment system for use on a mammalian body, comprising:
- elasticized wrap-around first and second garments for donning and releasably securing in a close-fitting fashion at generally different areas of the body;
- each of said garments comprising an outwardly facing surface at least a portion of which is adapted for accepting an area of releasable fasteners, and an under-layer having an inwardly facing surface to resist slippage when donned;
- first and second separate elasticized pieces, each of said separate pieces comprising at least one of said areas of releasable fasteners for application of said piece onto any said portion of said outwardly facing surfaces;
- wherein said area of releasable fasteners of said first elasticized piece releasably applied against said portion of said outwardly facing surface of said first and second garment, interconnects said first elasticized piece with said first and second garments in an operative therapeutic configuration; and
- wherein said second elasticized piece comprises an at least partially split-strap configuration having a first and second extension, said area of releasable fasteners of said second split-strap piece is comprised of a first and second region of releasable fasteners, said first extension comprises said first region and said second extension comprises said second region; and said second split-strap piece is adapted for application to at least one of said outwardly facing surfaces by utilizing said first and second region of releasable fasteners respectively located at each of an end of said first and second extensions.

8. The garment system of claim 7 further comprising, opposite said first and second extensions, a third and fourth extension, with said area of releasable fasteners of said second split-strap piece further comprising a third and fourth region of releasable fasteners, said third extension comprising said third region and said fourth extension comprising said fourth region; and wherein said second split-strap piece is further adapted for application to at least one of said outwardly facing surfaces by utilizing said third and fourth region of releasable fasteners respectively located at each of an end of said third and fourth extensions.

9. A garment system for use on a mammalian body, comprising:
- elasticized wrap-around first and second garments for donning and releasably securing in a close-fitting fashion at generally different areas of the body;
- each of said garments comprising an outwardly facing surface at least a portion of which is adapted for accepting an area of releasable fasteners, and an under-layer having an inwardly facing surface to resist slippage when donned;
- first and second separate elasticized pieces, each of said separate pieces comprising at least one of said areas of releasable fasteners for application of said piece onto any said portion of said outwardly facing surfaces;
- wherein said area of releasable fasteners of said first elasticized piece releasably applied against said portion of said outwardly facing surface of said first and second garment, interconnects said first elasticized piece with said first and second garments in an operative therapeutic configuration;
- said second elasticized piece adapted to be releasably applied against any said portion of said outwardly facing surface of either said first garment, said second garment, or both said first and second garment; and
- the garment system operatively donned in said close-fitting fashion, and wherein: said outwardly facing surface of each said garments comprises a woven fabric; said area of releasable fasteners each comprises an area having tiny flexible hooks for engagement with mating loop fabric; said under-layer comprises a polyether-polyurethane foam lining; and each of said elasticized pieces comprises a foam-lined woven fabric, an outer surface of which is adapted for accepting said area of releasable fasteners of another of said plurality of elasticized pieces such that said pieces may overlap in said operative therapeutic configuration.

10. A garment system for use on a mammalian body, comprising:
- elasticized wrap-around first and second garments for donning and releasably securing in a close-fitting fashion at generally different areas of the body;
- each of said garments comprising an outwardly facing surface at least a portion of which is adapted for accepting an area of releasable fasteners, and an under-layer having an inwardly facing surface to resist slippage when donned;
- first and second separate elasticized pieces, each of said separate pieces comprising at least one of said areas of releasable fasteners for application of said piece onto any said portion of said outwardly facing surfaces;
- wherein said area of releasable fasteners of said first elasticized piece releasably applied against said portion of said outwardly facing surface of said first and second garment, interconnects said first elasticized piece with said first and second garments in an operative therapeutic, configuration; and
- an elasticized limb garment comprising an under-layer having an inwardly facing surface to resist slippage and sized for wrapping around any portion of a limb of the body selected from the group consisting, of an arm, a shoulder, a hand, a leg, a hip, a foot, and a head; and wherein said area of releasable fasteners of said second elasticized piece is releasably applied to an outwardly facing surface of said limb garment and to said portion of said outwardly facing surface of either said first or second garment.

11. The garment system of claim 2 wherein said elasticized limb garment is selected from the group consisting of: a shoulder wrap, an upper-arm cuff, an elbow cuff, a forearm-area cuff, a wrist wrap, a hand sleeve wrap, an upper-leg cuff, a knee cuff, a shin-calf area cuff, an ankle wrap, a foot wrap, and a head cap; and wherein each said elasticized piece has a shape selected from the group consisting of a generally linear-elongated strap and an at least partially split-strap configuration having a first and second extension.

12. A therapeutic garment system for use on a mammalian body, comprising:
   elasticized wrap-around first and second unitary style garments for donning and releasably securing in a close-fitting fashion at generally different areas of the body;
   each of said unitary style garments comprising an outwardly facing surface adapted for accepting an area of releasable fasteners, and an under-layer having an inwardly facing surface to resist slippage when donned;
   first and second separate elasticized pieces, each of said separate pieces comprising at least one of said areas of releasable fasteners for application of said piece onto any of said outwardly facing surfaces;
   said area of releasable fasteners of said first elasticized piece releasably applied against said outwardly facing surface of each of said garments in an operative therapeutic configuration interconnecting said garments; and
   said second elasticized piece releasably applied against said outwardly facing surface of either said first garment, said second garment, or both said first and second garment.

13. A garment system for use on a mammalian body, comprising:
   elasticized wrap-around first and second garments for donning and releasably securing in a close-fitting fashion at generally different areas of the body;
   each of said garments comprising an outwardly facing surface adapted for accepting an area of releasable fasteners, and an under-layer having an inwardly facing surface to resist slippage when donned;
   first and second separate elasticized pieces, each of said separate pieces comprising at least one of said areas of releasable fasteners for application of said piece onto any of said outwardly facing surfaces;
   said area of releasable fasteners of said first elasticized piece releasably applied against said outwardly facing surface of each of said garments in an operative therapeutic configuration interconnecting said garment;
   said second elasticized piece adapted to be releasably applied against said outwardly facing surface of either said first garment, said second garment, or both said first and second garment; and
   wherein said elasticized second garment is selected from the group consisting of an elbow cuff, a forearm-area cuff, a wrist wrap, a hand sleeve wrap, an upper-leg cuff, a knee cuff, a shin-calf area cuff, an ankle wrap, a foot wrap, and a head cap; said elasticized wrap-around first garment is selected from the group consisting of an upper-torso garment, a lower-torso garment, and a full-torso garment; and said area of releasable fasteners of said first elasticized piece is comprised of a first and second region of releasable fasteners generally located at each of an end of said first elasticized piece for said application against said outwardly facing surfaces.

14. The garment system of claim 13 wherein: said first garment comprises said lower-torso garment and is donned around a lower-torso of the body by pulling over and around said lower-torso; and said second garment is donned by pulling said second garment around a portion of a limb of the body selected from the group consisting of a hand, a leg, a hip, a foot, and a head.

15. A therapeutic garment system for use on a mammalian body, comprising:
   elasticized wrap-around upper-torso and lower-torso garments for donning and releasably securing in a close-fitting fashion;
   each of said torso garments comprising an outwardly facing surface a substantial portion of which is adapted for accepting an area of releasable fasteners, and an under-layer having an inwardly facing surface to resist slippage when donned;
   first and second separate elasticized pieces, each comprising at least one of said areas of releasable fasteners, said first separate elasticized piece releasably applied, utilizing said area of releasable fasteners of said first separate, against said outwardly facing surface of said upper-torso garment in an operative therapeutic configuration said second elasticized piece adapted for releasable application against said portion of said outwardly facing surface of either said upper-torso garment, said lower-torso garment, or both said upper-torso and lower-torso garment; and
   wherein said upper-torso garment further comprises front and back panels releasably secured at each of a shoulder area of said panels and at each of a right and left side of said panels.

16. A garment system for use on a mammalian body, comprising:
   elasticized wrap-around first and second garments for donning and releasably securing in a close-fitting fashion at generally different areas of the body;
   each of said garments comprising an outwardly facing surface adapted for accepting an area of releasable fasteners, and an under-layer having an inwardly facing surface to resist slippage when donned;
   first and second separate elasticized pieces, each of said separate pieces comprising at least one of said areas of releasable fasteners for application of said piece onto any of said outwardly facing surfaces;
   said area of releasable fasteners of said first elasticized piece releasably applied against said outwardly facing surface of each of said garments in an operative therapeutic configuration interconnecting said garment;
   said second elasticized piece adapted to be releasably applied against said outwardly facing surface of either said first garment, said second garment, or both said first and second garment; and
   each said first and second elasticized piece has a shape selected from the group consisting of a generally linear-elongated strap and an at least partially split-strap configuration having a first and second extension; and said configuration operatively interconnecting said garments addresses an objective selected from the group consisting of: improve body posture by postural retraining; improve balance control of the body; improve movement control of the body; assist in body neuromotor re-education; assist in skeletal modeling of the body; support an injured area of the body; promote movement of at least a part of the body for athletic performance enhancement; assist in maintaining muscle tone by applying elasticized resistance to movement of a part of the body when in an environment wherein an effect from a gravitational force is less than the gravitational effects experienced on Earth; assist in stabilizing a joint of the body; and assist in maintaining, in a positional relationship to the body, a topically-applied therapeutic device.

17. A garment system for use on a mammalian body, comprising:
  elasticized wrap-around first and second garments for donning and releasably securing in a close-fitting fashion at generally different areas of the body;
  each of said garments comprising an outwardly facing surface a substantial portion of which is adapted for accepting an area of releasable fasteners, and an under-layer having an inwardly facing surface to resist slippage when donned;
  first and second separate elasticized pieces, each of said separate pieces comprising at least one of said areas of releasable fasteners for application of said piece onto said portion of said outwardly facing surfaces;
  wherein said area of releasable fasteners of said first elasticized piece releasably applied against said portion of said outwardly facing surface of said first and second garment, interconnects said first elasticized piece with said first and second garments in an operative therapeutic configuration;
  said second elasticized piece adapted to be releasably applied against said portion of said outwardly facing surface of either said first garment, said second garment, or both said first and second garment; and
  said second garment is a lower-torso garment comprising a waistband portion having a first and second end, said waistband portion interconnected with a thigh-wrap portion, said waistband ends adapted to be releasably secured in the body front; and said first of said elasticized piece comprises a foam-lined knitted fabric, an outer surface of which is adapted for accepting said area of releasable fasteners of another of said plurality of elasticized pieces.

18. A garment system for use on a mammalian body, comprising:
  elasticized wrap-around first and second garments for donning and releasably securing in a close-fining fashion at generally different areas of the body;
  each of said garments comprising an outwardly facing surface at least a portion of which is adapted for accepting an area of releasable fasteners, and an under-layer having an inwardly facing surface to resist slippage when donned;
  first and second separate elasticized pieces, each of said separate pieces comprising at least one of said areas of releasable fasteners for application of said piece onto any said portion of said outwardly facing surfaces;
  wherein said area of releasable fasteners of said first elasticized piece releasably applied against said portion of said outwardly facing surface of said first and second garment, interconnects said first elasticized piece with said first and second garments in an operative therapeutic configuration;
  said second elasticized piece adapted to be releasably applied against said portion of said outwardly facing surface of either said first garment, said second garment, or both said first and second garment; and
  said portion adapted for accepting said area of releasable fasteners substantially covers the whole of said outwardly facing surface of said first and second garments;
  and said area of releasable fasteners of said first elasticized piece is comprised of a first and second region of releasable fasteners.

19. A garment system for use on a mammalian body, comprising:
  elasticized wrap-around first and second garments for donning and releasably securing in a close-fitting fashion at generally different areas of the body;
  each of said garments comprising an outwardly facing surface adapted for accepting an area of releasable fasteners, and an under-layer having an inwardly facing surface to resist slippage when donned;
  first and second separate elasticized pieces, each of said separate pieces comprising at least one of said areas of releasable fasteners for application of said piece onto any of said outwardly facing surfaces;
  said area of releasable fasteners of said first elasticized piece releasably applied against said outwardly facing surface of each of said garments in an operative therapeutic configuration interconnecting said garment;
  said second elasticized piece adapted to be releasably applied against said portion of said outwardly facing surface of either said first garment, said second garment, or both said first and second garment; and
  the garment system operatively donned in said therapeutic configuration wherein: said area of releasable fasteners of said first elasticized piece is comprised of a first and second region of releasable fasteners; said first region releasably applied against said outwardly facing surface of said first garment and said second region releasably applied against said outwardly facing surface of said second garment.

20. A garment system for use on a mammalian body, comprising:
  elasticized wrap-around first and second garments for donning and releasably securing in a close-fitting fashion at generally different areas of the body;
  each of said garments comprising an outwardly facing surface a substantial portion of which is adapted for accepting an area of releasable fasteners, and an under-layer having an inwardly facing surface to resist slippage when donned;
  first and second separate elasticized pieces, each of said separate pieces comprising at least one of said areas of releasable fasteners for application of said piece onto said portion of said outwardly facing surfaces;
  wherein said area of releasable fasteners of said first elasticized piece releasably applied against said portion of said outwardly facing surface of said first and second garment, interconnects said first elasticized piece with said first and second garments in an operative therapeutic configuration;
  said second elasticized piece adapted to be releasably applied against said portion of said outwardly facing surface of either said first garment, said second garment, or both said first and second garment; and
  the garment system operatively donned in said therapeutic configuration, such that: a partial overlap of said first and second garments results; and a partial overlap between said second elasticized piece and said first elasticized piece results.

21. A garment system for use on a mammalian body, comprising:
  elasticized wrap-around first and second garments for donning and releasably securing in a close-fitting fashion at generally different areas of the body;

each of said garments comprising an outwardly facing surface a substantial portion of which is adapted for accepting an area of releasable fasteners, and an under-layer having an inwardly facing surface to resist slippage when donned;

first and second separate elasticized pieces, each of said separate pieces comprising at least one of said areas of releasable fasteners for application of said piece onto said portion of said outwardly facing surfaces;

wherein said area of releasable fasteners of said first elasticized piece releasably applied against said portion of said outwardly facing surface of said first and second garment, interconnects said first elasticized piece with said first and second garments in an operative therapeutic configuration;

said second elasticized piece adapted to be releasably applied against said portion of said outwardly facing surface of either said first garment, said second garment, or both said first and second garment; and said outwardly facing surface of each said garments comprises a knitted fabric; said area of releasable fasteners each comprises an area having tiny flexible hooks for engagement with mating loop fabric; said under-layer comprises a foam lining; and each of said elasticized pieces comprises a foam-lined knitted fabric.

22. A garment system for use on a mammalian body, comprising:

elasticized wrap-around first and second garments for donning and releasably securing in a close-fitting fashion at generally different areas of the body;

each of said garments comprising an outwardly facing surface a substantial portion of which is adapted for accepting an area of releasable fasteners, and an under-layer having an inwardly facing surface to resist slippage when donned;

first and second separate elasticized pieces, each of said separate pieces comprising at least one of said areas of releasable fasteners for application of said piece onto said portion of said outwardly facing surfaces;

wherein said area of releasable fasteners of said first elasticized piece releasably applied against said portion of said outwardly facing surface of said first and second garment, interconnects said first elasticized piece with said first and second garments in an operative therapeutic, configuration;

said second elasticized piece adapted to be releasably applied against said portion of said outwardly facing surface of either said first garment, said second garment, or both said first and second garment; and wherein said first garment is an upper-torso garment and said second garment is a lower-torso garment, both of which are operatively donned in said therapeutic configuration such that no spacing effectively exists between a bottom perimeter of the upper-torso garment and an upper waistband perimeter of said lower-torso garment.

23. A garment system for use on a mammalian body, comprising:

elasticized wrap-around first and second garments for donning and releasably securing in a close-fitting fashion at generally different areas of the body;

each of said garments comprising an outwardly facing surface a substantial portion of which is adapted for accepting an area of releasable fasteners, and an under-layer having an inwardly facing surface to resist slippage when donned;

first and second separate elasticized pieces, each of said separate pieces comprising at least one of said areas of releasable fasteners for application of said piece onto said portion of said outwardly facing surfaces;

wherein said area of releasable fasteners of said first elasticized piece releasably applied against said portion of said outwardly facing surface of said first and second garment, interconnects said first elasticized piece with said first and second garments in an operative therapeutic configuration;

said first garment is an upper-torso garment and further comprises front and back panels integral at each of a shoulder area thereof and releasably secured at each of a right and left side of said panels using said second elasticized piece and a third separate piece;

a size-tailoring indicia extends along, in offset proximity to, at least a portion of a perimeter of said front panel to aid in trimming material therefrom; and said releasable fasteners are selected from the group consisting of: an area having tiny flexible hooks for engagement with mating loop fabric; an area comprising an array of snaps; an area comprising an array of D-rings; an area comprising an array of small buckles; and an area comprising an array of hook-and-eye enclosures.

\* \* \* \* \*